United States Patent [19]

Burke et al.

[11] Patent Number: 4,933,483

[45] Date of Patent: Jun. 12, 1990

[54] MANUFACTURE OF 5-CYANOVALERIC ACID AND ITS ESTERS

[75] Inventors: Patrick M. Burke; James B. Sieja, both of Wilmington, Del.

[73] Assignee: E. I. Du Pont de Nemours and Company, Wilmington, Del.

[21] Appl. No.: 283,158

[22] Filed: Dec. 12, 1988

[51] Int. Cl.$^5$ .................. C07C 120/00; C07C 121/16
[52] U.S. Cl. ..................................... 558/353; 558/441
[58] Field of Search ........................................ 558/353

[56] References Cited

U.S. PATENT DOCUMENTS

| | | | |
|---|---|---|---|
| 3,546,269 | 12/1970 | Wakamatsu et al. | 558/353 |
| 4,060,543 | 11/1977 | Weitz et al. | 558/353 |
| 4,508,660 | 4/1985 | Sieja | 558/353 |

FOREIGN PATENT DOCUMENTS 1497046  1/1978  United Kingdom ................ 558/353

OTHER PUBLICATIONS

Fell, et al.; Chem. Ztg., 111, pp. 317–323 (1987).
Falbe; "New Syntheses with Carbon Monoxide", (1980), p. 252, Springer-Verlag, Berlin, Heidelberg, N.Y.
Imyanitov, et al.; "Organic Chemistry and Technology", Khimicheskaya Promyshlennost, 19, (1987), pp. 4–7.

Primary Examiner—Joseph Paul Brust

[57] ABSTRACT

Manufacture of 5-cyanovaleric acid and its esters by carbonylation of pentenenitriles from a mixture consisting essentially of pentenenitrile, CO and at least one compound of the formula R'OH, where R is hydrogen or alkyl of 1 to 6 carbon atoms.

8 Claims, No Drawings

MANUFACTURE OF 5-CYANOVALERIC ACID AND ITS ESTERS

FIELD OF THE INVENTION

The invention relates to an improved process for the manufacture of 5-cyanovaleric acid and its esters from pentenenitriles in high selectivity to this linear product.

BACKGROUND

Processes for the preparation of 5-cyanovaleric acid from pentenenitriles by carbonylation in the presence of cobalt carbonyl catalysts are known. See, for example, U.S. Pat. No. 4,508,660 to Sieja where the reaction is carried out in a sulfone solvent, and U.S. Pat. No. 4,060,543 to Weitz, et al., where the reaction is carried out in the presence of basic heterocyclic compounds having a 5-membered or 6-membered nitrogen-containing ring, for example pyridine.

It seems to be recognized in the art that the presence of pyridine in a carbonylation reaction mixture provides an increased yield in the straight chain isomers —See *Organic Chemistry and Technology*, New Method of Production of Adipic Acid, N. S. Imyanitov and E. N. Rakhlina, Khimicheskaya Promyshlennost, Vol. 19, No. 12, pp. 4–7, 1987 and *Chem. Ztg.* 111 no 11:317–23 (1987) Hydrocarboxylation of Unsaturated Carboxylic Acids and Esters with Cobalt Carbonyl/Pyridine Complex Catalyst Systems by Bernhard Fell, Institute for Technical Chemistry and Petrochemistry of the RWTH Aachen, and Zilin Jin, Dalian Institute of Technology, Dalian/Peoples Republic of China, and *New Syntheses with Carbon Monoxide*, edited by J. Falbe; page 252, Springer-Verlag, Berlin Heidelberg, N.Y., 1980.

SUMMARY OF THE INVENTION

It has now been found that 5-cyanovaleric acid and its esters can be obtained in high yield from any pentenenitrile at a high selectivity, without the use of pyridine type promoters, and without the use of sulfone solvents. The process offers an advantage over the prior art processes, in that there are fewer components to separate from the reacted mixture; furthermore the yields of 5-cyanovaleric acid are higher when operating without a pyridine type promoter.

More particularly a high yield process for the preparation of a compound having the formula:

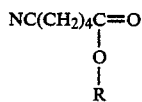

where R is hydrogen or an alkyl radical having 1 to 6 carbon atoms, has been discovered. The process comprises reacting a mixture consisting essentially of pentenenitrile, carbon monoxide, at least one compound having the formula: R'OH, where R' is hydrogen or an alkyl radical having 1 to 6 carbon atoms, and optionally a minor amount of one or more cosolvents selected from the class consisting of lower alkyl nitriles i.e. those having 1 to 6 carbon atoms, with a cobalt containing carbonylation catalyst, at a temperature in the range of about 130° to 220° C. and at a pressure of about 1500 to 8000 psi.

The compound R'OH acts as a reactant, and also as a solvent.

In most instances the amount of cobalt containing carbonylation catalyst in the reaction should be about 0.5 to 5 parts by weight per 100 parts of pentenenitrile.

DETAILED DESCRIPTION

The cobalt containing carbonylation catalysts useful in the process of this invention are cobalt compounds including cobalt salts of Bronsted acids, carbon monoxide derivatives of cobalt and organometallic cobalt compounds. It is believed that negatively charged cobalt is the active catalyst species and that it can be formed in situ from a variety of compounds such as those of the general types discussed above. Suitable salts are cobaltous and cobaltic chloride, iodide, bromide, propionate, butyrate, isobutyrate, acetate, carbonate, benzoate, valerate, 5-cyanovalerate, pentenoate, and hydroxide. Suitable organometallic cobalt compounds include dicyclopentadienyl cobalt, π-allyl cobalttricarbonyl, and π-crotyl cobalttricarbonyl. Compounds which are carbon monoxide derivatives of cobalt include dicobalt octacarbonyl, cobalt nitrosyltricarbonyl, cyclopentadienylcobalt dicarbonyl and tetracobaltdodecacarbonyl.

The process of this invention can be used to convert any of the pentenenitrile isomers to 5-cyanovaleric acid or its esters, but 3-pentenenitrile and 4-pentenenitrile are somewhat more satisfactory than 2-pentenenitrile, in that the latter compound tends to yield more valeronitrile.

The R'OH compound in the reaction mixture will usually be water or methanol, or a mixture of water and methanol. The rate of the reaction is slower when no water is present in the reaction mixture. The R' radical can also be ethyl, propyl, butyl, pentyl, or hexyl in which case the reaction product will be the corresponding ester. It is desirable that the amount of the R'OH compound in the reaction mixture be at least stoichiometrically equivalent to the amount of pentenenitrile, and the R'OH compound may be present in large excess.

One or more cosolvents selected from the class consisting of alkyl nitriles having 1 to 6 carbon atoms, (for example, butyronitrile, propionitrile, etc.), may be included in the reaction mixture The cosolvents can be present in amounts from 1 to 20% by weight of the reaction mixture.

The reaction is carried out at a temperature in the range of about 130° to 220° C. and at a pressure of about 1500 to 8000 psi.

EXAMPLE 1

Hydrocarboxylation of 3-Pentenenitrile in Water

A 300 ml Hastelloy-C mechanically stirred autoclave was flushed with nitrogen and then with high purity carbon monoxide. It was then charged with a mixture of 12.15 grams (150 mmole) of 3-pentenenitrile (3-PN) and 150 grams of water. The autoclave was pressured with CO to 2000 psi and then heated to 160° C. The reaction was initiated by injecting into the autoclave a solution made by dissolving 5.12 grams (30 mmoles) of dicobalt octacarbonyl in 12.15 grams (150 mmole) 3PN. The autoclave pressure was then immediately adjusted to 3000 psi with CO by means of a regulator valve. Carbon monoxide was continuously fed to the autoclave from a 500 ml reservoir at an initial pressure of 4450 psi so as to maintain the total pressure constant at 3000 psi. The reaction was allowed to run for a total of 5 hours after which it was cooled to 20° C. The excess CO was vented through a control valve and the product was discharged. The autoclave was washed first with 150 ml methanol at 100° C. under autogenous pressure and then with 150 ml tetrahydrofuran at room temperature.

The product and washes from the autoclave were combined, 5.0 grams of tetradecane internal gas chromatographic (GC) standard was added and the solution was diluted to 500 ml with methanol. A sample of this solution, esterified by heating in a sealed vial at 90° C. for 14 hours with trimethylorthoformate and sulfuric acid esterification catalyst, was analyzed as the methyl esters by capillary gas chromatography. Product accounting (moles of all products recovered divided by moles 3PN charged) was 95.5%. Correcting to 100% accounting, the analysis showed 23% conversion of pentenenitrile (all isomers), 78.7% yield of 5-cyanovaleric acid (5CVA), 6.0% yield of adipic acid (AA), 6.13% yield of branched C6 acids (2-methyl-4-cyanobutryic acid, 2-cyanovaleric acid, 2-methylglutaric acid and ethylsuccinic acid), 8.6% valeronitrile and 0.5% yield of valeric acid. Thus the total yield of linear product (5CVA+AA) is 84.7% and the linearity is 93.2% where $$\text{linearity} = \frac{\text{linear difunctional products}}{\text{all difunctional products}}.$$

When the esterification was run for a shorter time (30 min) the accounting was 95.3% and the yield of adipic acid present was much less (2.0%) and that of 5-cyanovaleric acid correspondingly greater (81.4%) indicating that, at longer esterification time, the adipic acid is largely formed by solvolysis of 5CVA during the esterification and not during the carbonylation reaction.

CONTROL EXAMPLES (PRIOR ART) (U.S. PAT. NO. 4,060,543) A. Carbonylation of 3PN in Tetrahydrofuran with Co catalyst and Pyridine Promoter The experiment in Example 1 was repeated except that the autoclave was initially charged with 24.3 grams 3PN, 5.0 grams tetradecane (internal gas chromatographic (GC) standard), 81 grams tetrahydrofuran, (THF) 24 grams methanol and 4.2 grams cobalt carbonyl. The mixture was heated to 160° C. under a cold CO pressure of 2000 psi. A solution of 7.9 grams pyridine in 9 grams THF was injected and the pressure was adjusted to 3000 psi. The reaction was allowed to proceed for 5 hours. Analysis showed 61.5% nitrile conversion, 72.3% methyl-5-cyanovalerate (M5CV), 15.5% branched C6 esters and 11.8% valeronitrile. Linearity was 82.4% and product accounting was 96.2%. (The patent reported an isolated yield of 70.1% M5CV under the same conditions).

The experiment in Example A was repeated except that the methanol was replaced by an equimolar amount of water (13.5 grams) and the reaction was allowed to run for 2.5 hours (CO uptake ceased). GC analysis after esterification of the acids showed 54.4% nitrile conversion and the following yields: 67.4% 5CVA+AA, 7.0% C6 branched acids and 24.7% valeronitrile+valeric acid. The mass balance was 100% and the linearity was 90.6%. The patent reported a 5CVA yield of 61.4% under the same conditions.

B. Carbonylation of 3PN in Toluene with Co Catalyst and Pyridine promoter (BP No. 1,497,046, to ICI)

The experiment in Example 1 was repeated except that the autoclave was charged with 12.15 grams 3PN, 45 grams toluene and 3.8 grams pyridine. Reaction was initiated by adding a solution of 5.97 grams of cobalt acetate tetrahydrate in 18 grams methanol. The reaction was allowed to run until CO uptake ceased (1.5 hours at 160° C. and 3000 psi). Analysis of the product showed 93% nitrile conversion and the following yields: 56.5% M5CV, 15.4% branched esters, and 26.1% valeronitrile. Linearity was 78.6% and product accounting was 93.2%.

EXAMPLE 2 Hydrocarboxylation of 3PN in water—Lower PN/water ratio

The experiment in Example 1 was repeated except that the autoclave was charged with 150 ml water alone and the reaction was initiated by injecting a solution made from 5.2 grams of cobalt octacarbonyl in 12.2 grams of 3PN. Gas chromatographic analysis showed 39.4% nitrile conversion and 93% product accounting. The following yields (normalized to 100% accounting) were obtained: 88.7% 5CVA+AA, 3.7% branched C6 acids and 7.6% valeronitrile (linearity: 96%).

EXAMPLE 3 Hydrocarboxylation of 3PN in water/n-butyronitrile mixtures

The experiment in Example 1 was repeated except that the autoclave was charged with a mixture of 109 ml water and 31 ml butyronitrile (450 mmoles) and the reaction was initiated by injecting a solution made from 5.2 grams of cobalt octacarbonyl in 12.2 grams 3-pentenenitrile. Gas chromatographic analysis of the product showed 48.3% nitrile conversion and 92.3% product accounting. The following yields, normalized to 100% accounting, were obtained: 90.4% 5CVA+AA, 3.2% branched C6 acids and 6.4% valeronitrile. Linearity was 96.6%.

EXAMPLE 4 Hydrocarboxylation of 3PN in water/n-propionitrile mixtures

The experiment in Example 1 was repeated except that the autoclave was charged with 139.3 ml water and 8.3 grams (150 mmole) propionitrile and the reaction was initiated by injecting a solution made from 5.2 grams of cobalt octacarbonyl in 12.2 grams 3PN. Gas chromatographic analysis of the product showed 36.3% PN conversion and 85% product accounting. Yields, based on 100% accounting were 92.6% 5CVA+AA, 3.3% branched C6 acids and 4.2% valeronitrile. Linearity was 96.6%.

EXAMPLE 5 Carbomethoxylation of 3PN in anhydrous Methanol

The experiment in Example 1 was repeated except that the autoclave was charged with 12.2 grams of 3PN and 150 ml anhydrous methanol (sodium dried, <0.02% water) and the reaction was initiated by injecting a solution made from 5.1 grams of cobalt carbonyl and 12.2 grams of 3PN. The reaction was run for a total of 1 hour. Gas chromatographic analysis of the product as acids, showed only 2.2% conversion of pentenenitrile, 93% product accounting and the following yields (as acids, normalized to 100% accounting): 65% AA+5CVA, 27.1% branched C6 acids and 7.9% valeronitrile. Linearity is 70.6%.

EXAMPLE 6 Carbomethoxylation of 3PN in Methanol in the Presence of water

The experiment in example 1 was repeated except that the autoclave was charged with 150 ml of methanol solution containing 10.8 grams water (600 mmole). The reaction was run for a total of 5 hours at 160° C. and 3000 psi total pressure. Analysis, after esterification, showed 85.3% nitrile conversion and the following normalized yields: 80.7% M5CV+AA, 3.7% branched C6 esters and acids, and 15.7% valeronitrile.

(a) 1:1 water to PN mole ratio.

The experiment in example 5 was repeated except that 5.4 grams (300 mmole) water was added to the anhydrous methanol. The reaction was also run for 1 hour. Gas chromatographic analysis of the product before esterification showed 28.6% conversion of pentenenitrile 87% product accounting and the following yields (normalized to 100% accounting): 69.1% M5CV, 7.1% 5-cyanovaleraldehyde dimethylacetal, 0.93% dimethyl adipate, 7.3% branched C6 esters and 16.5% valeronitrile. Linearity is 92.4%. Comparison with example 5 shows that both rate and linearity are markedly improved by addition of water to the methanol.

(b) In the Presence of a water Scavenger (Trimethylorthoformate, TMOF)

The experiment in example 1 was repeated except that the water was replaced with 150 ml of methanol solution containing 15.9 grams (150 mmole) of trimethylorthoformate (TMOF). The reaction was initiated by adding a solution made from 1.3 grams of cobalt carbonyl in 12.2 grams of 3-pentenenitrile. The reaction was run for a total of 5 hours at 160° C. and 3000 psi total pressure. Analysis showed only 10.0% pentenenitrile conversion and the following normalized yields: 85.6% M5CV, 11.9% branched C6 esters, and 2.5% valeronitrile (linearity is 87.8%).

(c) 2.1 water PN mole ratio

When the TMOF in example 6(b) was replaced with 10.8 grams of water in an otherwise identical experiment, the pentenenitrile conversion increased to 85.3% and the following normalized yields were obtained: 80.7% 5CVA+AA, 3.7% branched esters and acids, and 15.7% reduction (valeronitrile and valeric acid) (linearity is 96.6%).

(d) Equimolar Methanol and Water

When the TMOF-Methanol in example 6(b) was replaced with 46 grams water (2.55 mole) and 81.8 grams methanol (2.55 mole), the pentenenitrile conversion after 5 hours was 53.4% and the normalized yields were 90.1% 5CVA+AA, 3.31% branched acids and esters and 6.6% reduction (valeronitrile and valeric acid) (linearity is 96.4%).

(e) With 9:1 Water to Methanol Ratio

When the TMOF-Methanol in (b) was replaced with a mixture of 120 ml water (6.67 moles) and 30 ml methanol (0.74 moles) and the catalyst concentration was increased to 2.6 grams, the pentenenitrile conversion after 5 hours was 36.3% and the following normalized yields were obtained: 91.7% 5CVA+AA, 4.5% branched acids and esters and 3.9% reduction (valeronitrile and valeric acid). (Linearity is 96.3%).

We claim:

1. A high yield process for the preparation of a compound having the formula:

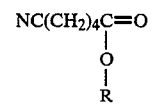

where R is hydrogen of an alkyl radical having 1 to 6 carbon atoms, which comprises reacting a mixture consisting essentially of pentenenitrile, carbon monoxide, at least one compound having the formula: R'OH, where R' is hydrogen or an alkyl radical having 1 to 6 carbon atoms, with a cobalt containing carbonylation catalyst, at a temperature in the range of about 130° to 220° and at a pressure of about 1500 to 8000 psi, where said R'OH is present in the mixture in an amount at least stoichiometrically equivalent to the amount of pentenenitrile, said cobalt containing carbonylation catalyst is present in the amount of 0.5 to 5 parts by weight per 100 parts of pentenenitrile, and the R in the product is the same as the R' in the R'OH compound.

2. The process of claim 1 in which R is hydrogen and R' is hydrogen, and the cobalt catalyst is dicobalt octacarbonyl.

3. The process of claim 1 in which there are two compounds having the formula R'OH in the reaction mixture.

4. The process of claim 3 in which one of the compounds is water and the other is methanol.

5. The process of claim 1 in which the pentene nitrile is 3-pentenenitrile.

6. The process of claim 1 in which the pentene nitrile is 2-pentenenitrile.

7. The process of claim 1 in which the pentene nitrile is 4-pentenenitrile.

8. The process of claim 1 in which R' is hydrogen.

* * * * *